United States Patent
Hasegawa et al.

(10) Patent No.: US 9,488,519 B2
(45) Date of Patent: Nov. 8, 2016

(54) MEASURING INSTRUMENT USING LIGHT BEAM

(71) Applicant: SAMCO INC., Kyoto-shi, Kyoto (JP)

(72) Inventors: Kiyoshi Hasegawa, Otokuni-gun (JP); Hiroshi Kawamura, Kyoto (JP); Peter Wood, San Jose, CA (US)

(73) Assignee: SAMCO INC., Kyoto (JP)

( * ) Notice: Subject to any disclaimer, the term of this patent is extended or adjusted under 35 U.S.C. 154(b) by 0 days.

(21) Appl. No.: 14/730,762

(22) Filed: Jun. 4, 2015

(65) Prior Publication Data
US 2015/0355016 A1 Dec. 10, 2015

(30) Foreign Application Priority Data

Jun. 10, 2014 (JP) ................. 2014-119392

(51) Int. Cl.
*G01N 21/55* (2014.01)
*G01J 1/02* (2006.01)
*G01J 1/42* (2006.01)
*G01N 21/84* (2006.01)

(52) U.S. Cl.
CPC ............ *G01J 1/0238* (2013.01); *G01J 1/4257* (2013.01); *G01N 21/55* (2013.01); *G01N 2021/8427* (2013.01); *G01N 2201/025* (2013.01); *G01N 2201/1087* (2013.01)

(58) Field of Classification Search
CPC combination set(s) only.
See application file for complete search history.

(56) References Cited

U.S. PATENT DOCUMENTS 8,325,344 B2 * 12/2012 Lee .................. B41F 33/0036
356/406

FOREIGN PATENT DOCUMENTS

JP 2006330210 A 12/2006

OTHER PUBLICATIONS

Benferhat, Ramdane, "Plasma Dry Etch End-Point Monitor, DIGILEM," Horiba, Ltd., [Searched Jun. 4, 2014], Internet.
"Optical End-Point Detectors," Oxford Instruments plc, [searched Jun. 4, 2014, Internet.

* cited by examiner

*Primary Examiner* — Tri T Ton
(74) *Attorney, Agent, or Firm* — Oliff PLC

(57) ABSTRACT

The present invention provides a light beam measuring instrument that can securely receive light reflected by a sample. The light beam measuring instrument 1 includes an optical axis tilting mechanism 13 that includes a first tilting mechanism 131 and a second tilting mechanism 132. From the optical axis A1 of irradiation light beam emitted from a light beam source 112, the first tilting mechanism 131 tilts the optical axis A1 about the first tilting axis T1. The second tilting mechanism 132 tilts the optical axis A1 about the second tilting axis T2. The light beam measuring instrument 1 can receive the light reflected by the semiconductor chip C by means of operation of the optical axis tilting mechanism 13 even if the light reflected by the semiconductor chip C is tilted. Accordingly, this apparatus can securely perform measurement or inspection using the light beam.

9 Claims, 7 Drawing Sheets

MEASURING INSTRUMENT USING LIGHT BEAM

TECHNICAL FIELD

The present invention relates to a measuring instrument using light beam (which will be referred to as "light beam measuring instrument") that irradiates a sample with a light beam, such as laser light beam, detects the light beam reflected by the sample, and performs measurement or inspection based on the detection.

BACKGROUND ART

Light beam measuring instruments are used in various situations. Among them are included, for instance, quality inspections of semiconductor products, in which semiconductor chips are inspected whether they are correctly formed or whether wiring is correctly made, and reverse engineering of a competitor's semiconductor circuit. An end-point detector (EPD) can be regarded as a type of light beam measuring instrument for determining whether etching reaches a desired depth or not by means of light reflected from the bottom surface of etching or of interference of the lights reflected from the top surface and reflected from the bottom surface of etching during etching by plasma or the like.

CITATION LIST

Patent Literature

[Patent Literature 1] JP 2006-330210 A

Non Patent Literature

[Non Patent Literature 1] Ramdane Benferhat, "Plasma dry etch end-point monitor, DIGILEM", [online], Horiba, Ltd., [searched Jun. 4, 2014], Internet
[Non Patent Literature 2] "Optical end-point detectors", [online], Oxford Instruments plc, [searched Jun. 4, 2014], Internet

SUMMARY OF INVENTION

Technical Problem

It is not always possible to visually confirm beforehand or predict the position of the part of a sample to be irradiated with a light beam. For instance, in the case of inspecting or measuring a surface of a semiconductor chip molded in a resin package, the resin mold of the package is etched by plasma or other means to reveal the semiconductor chip, which is then irradiated with a light beam. If the semiconductor chip is tilted in the package, the reflected light deviates, and the light beam may not return to the light beam measuring instrument. Normally in such an instrument for etching a resin package, the light beam is delivered from outside of the etching chamber (vacuum chamber) through a small window of the etching chamber. This inevitably leads to an elongated distance between the light beam source and the semiconductor chip (sample), and even a slight tilt of the semiconductor chip surface and the resultant deviation of the reflected light prevent the reflected light beam from returning to the light beam measuring instrument.

In view of such a problem in the conventional light beam measuring instrument, the present invention has an object to provide a light beam measuring instrument that can securely receive the light beam reflected by a sample.

Solution to Problem

A device according to the present invention made to solve the problem is a light beam measuring instrument including a light beam source for emitting a light beam toward an object, and a light beam detector for detecting the light beam reflected by a surface of the object, the light beam measuring instrument further including:

a first optical-axis-tilting mechanism configured to tilt the light beam source about a first tilting axis lying in a plane unparallel to the optical axis of the light beam emitted from the light beam source; and a second optical-axis-tilting mechanism configured to tilt the light beam source about a second tilting axis lying in the plane and unparallel to the first tilting axis.

The light beam measuring instrument according to the present invention can tilt, in any degree, the light beam source by means of the first optical-axis-tilting mechanism and the second optical-axis-tilting mechanism. Accordingly, the direction of the light beam emitted from the light beam source, i.e., the direction of the optical axis, can be tilted as necessary, and the light beam reflected by the object can be correctly returned to the light beam detector.

Preferably, the light beam measuring instrument according to the present invention includes not only the mechanism of tilting the optical axis but also a translation mechanism configured to translate (or laterally move) the optical axis of the light beam emitted from the light beam source. If the direction of the optical axis is tilted by the optical axis tilting mechanism, the position on the object irradiated with the light beam moves. Even in this case, the translation mechanism can restore the irradiation position, or can fix the irradiation position on the object. The translation mechanism may be either a mechanism that translates (or moves) the light beam source, or a mechanism that translates (or moves) the object.

It is preferred that, in order to perform the fixation of the irradiation position automatically, an irradiation position controller be provided to drive the translation mechanism. The irradiation position controller may perform the control by analyzing the position or shape of the irradiated light beam on the object using an image, or by detecting the irradiation (tilting) angle of the light beam. In the analysis and determination of the irradiation position using an image, specifically, an intensity of the light in the image can be analyzed.

The optical-axis-tilting mechanism may be a cylindrical type two-axis gonio-stage including two sets of sliding partial cylindrical surfaces for the first tilting axis and the second tilting axis. Alternatively, the mechanism may be a plane tilting type two-axis gonio-stage in which a plane is tilted in two directions by moving two points other than a pivot of the plane vertically (or parallel to the optical axis) while fixing the pivot. Otherwise, a tilting mechanism using a ball joint or a universal joint may be employed.

Advantageous Effects of Invention

The light beam measuring instrument according to the present invention can always return and receive the light beam reflected by a surface of the object, even if the surface is tilted. Accordingly, this instrument can securely perform proper measurement or inspection.

When a mechanism for translating the light beam source is used, the object need not be moved when tilting the optical axis of a light beam in the light beam measuring instrument according to the present invention. In this case, light beam measurement or inspection can be performed while the object is undergoing a process, such as etching or the like.

DESCRIPTION OF EMBODIMENTS

A first embodiment is hereinafter described where a light beam measuring instrument according to the present invention is applied to an apparatus of inspecting a surface of a semiconductor device or the like with reference to FIG. 1 to FIG. 3.

Figure 1:
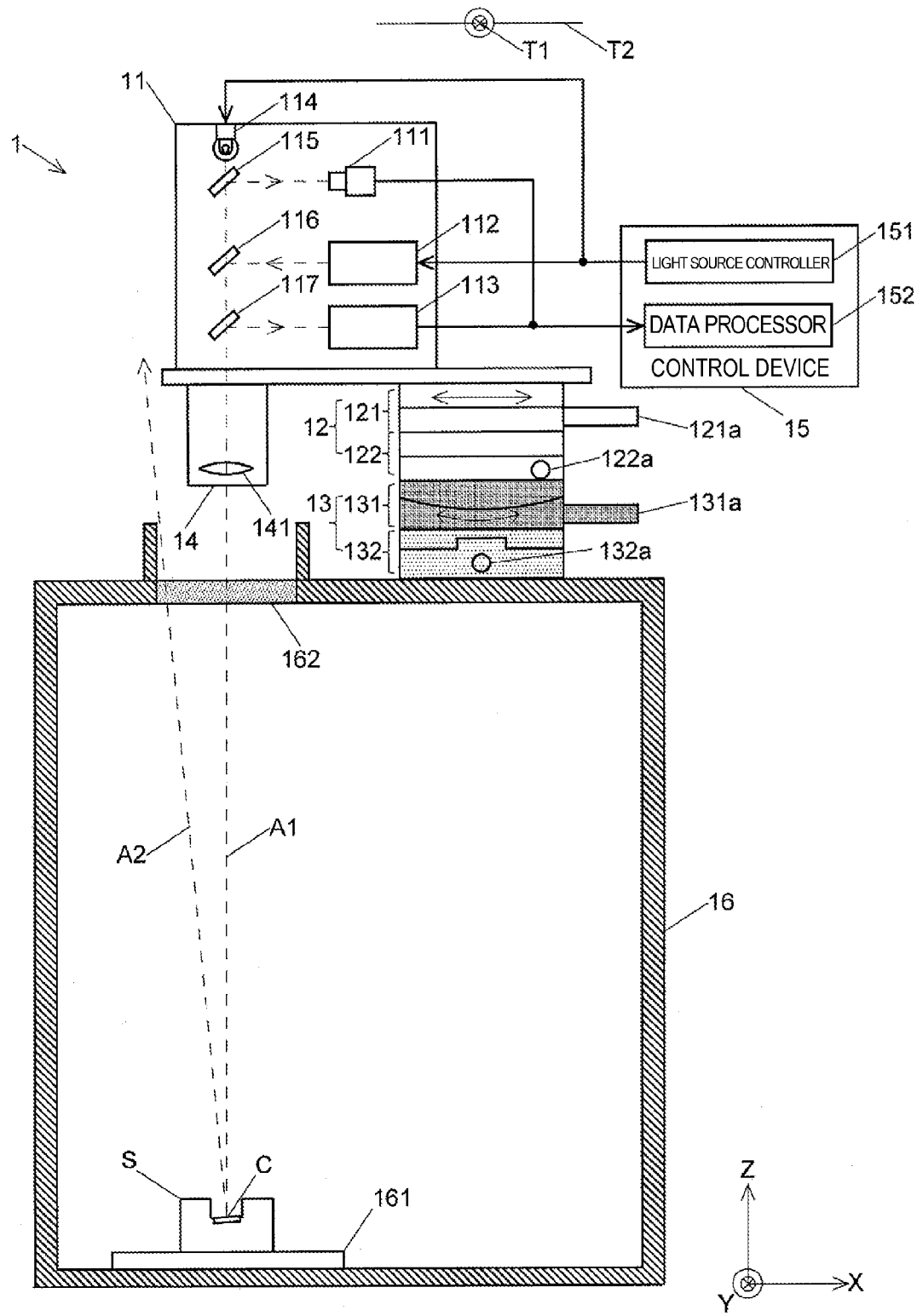
FIG. 1 is an overall configuration diagram of a surface inspection apparatus according to a first embodiment of the present invention.

FIG. 1 is a schematic overall configuration diagram of a surface inspection apparatus 1 according to this embodiment. The surface inspection apparatus 1 includes a main body 11, an XY stage 12, a cylindrical type two-axis gonio-stage 13, a laser light condenser 14, a control device 15 and a vacuum chamber 16. The cylindrical type two-axis gonio-stage 13 (hereinafter, simply referred to as "two-axis gonio-stage 13") is an optical axis tilting mechanism of the present invention. A sample stage 161 on which a resin package semiconductor sample S to be inspected is mounted is provided at the bottom of the vacuum chamber 16. On the ceiling of the vacuum chamber 16 above the stage, a sample window 162 for projecting light to the sample S and receiving light reflected by the sample S is provided. In actuality, the vacuum chamber 16 forms a part of a plasma processing apparatus (plasma processing chamber). This surface inspection apparatus 1 inspects the surface of a semiconductor chip C while gradually etching the resin package of the sample S and the semiconductor chip C molded in the package.

The main body 11 is mounted on the XY stage 12 which is, in turn, mounted on the two-axis gonio-stage 13, both of which are disposed aside of the sample window 162 of the vacuum chamber 16. Though, in FIG. 1, the XY stage 12 is shown mounted on the two-axis gonio-stage 13, the two-axis gonio-stage 13 may be alternatively mounted on the XY stage 12. The control device 15 may be integrated with the main body 11, or it may be provided separately. In the separately provided case, the control device 15 can be constructed by dedicated software installed in a personal computer. An input unit (not shown) and an output unit (not shown) are connected to the main body 11. Alternatively, the input unit and the output unit may be connected to the control device 15.

The main body 11 includes a CCD camera 111, a laser light source 112 consisting of a laser diode, a laser light detector 113, a visible light source 114, and half mirrors 115, 116 and 117. The half mirrors 115 to 117 are disposed in series just above the laser light condenser 14. The visible light source 114 is disposed behind the half mirrors 115, 116 and 117 (on the opposite side of the laser light condenser 14). The CCD camera 111, the laser light source 112 and the laser light detector 113 are disposed so as to face the reflective surfaces of the half mirrors 115, 116 and 117, respectively. The laser light condenser 14 includes a condenser lens 141.

Figure 2:
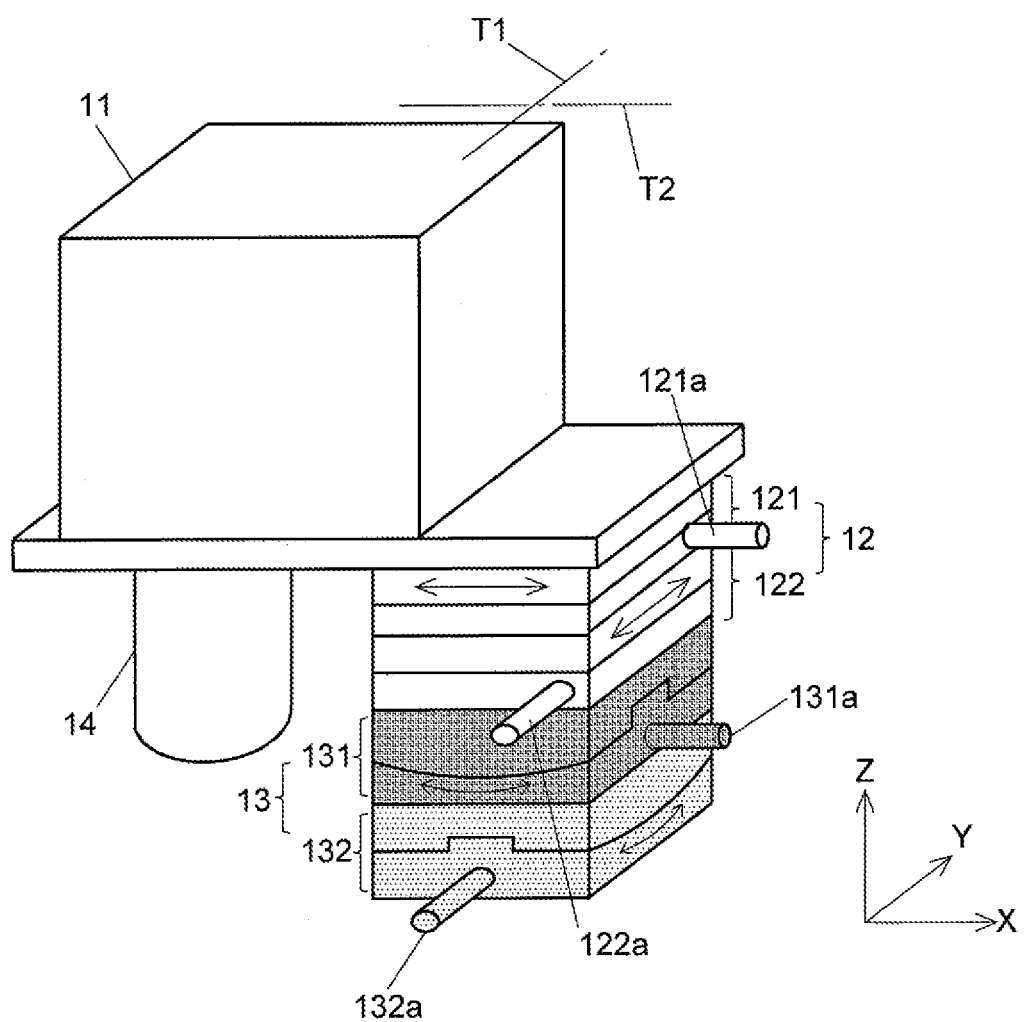
FIG. 2 is a perspective view of a main part of the surface inspection apparatus according to the first embodiment of the present invention.

FIG. 2 shows a perspective view of the main body 11, the XY stage 12, the two-axis gonio-stage 13 and the laser light condenser 14 of the surface inspection apparatus 1 according to this embodiment.

The XY stage 12 includes an X stage 121 and a Y stage 122. The X stage 121 and the Y stage 122 are provided with an X direction translation handle 121a and a Y direction translation handle 122a, respectively. Rotating the X direction translation handle 121a causes the main body 11 to translate in the X direction. Rotating the Y direction translation handle 122a causes the main body 11 to translate in the Y direction.

The two-axis gonio-stage 13 includes a first gonio-stage 131 and a second gonio-stage 132. The first gonio-stage 131 and the second gonio-stage 132 include a first rotation handle 131a and a second rotation handle 132a. The first gonio-stage 131 and the second gonio-stage 132 have a mechanism for sliding cylindrical surfaces centered on a first tilting axis T1 parallel to the Y axis and a second tilting axis T2 parallel to the X axis, respectively. The first tilting axis T1 and the second tilting axis T2 are depicted at upper parts of FIG. 1 and FIG. 2. Rotating the first rotation handle 131a causes the main body 11 to pivot about the axis T1. Rotating the second rotation handle 132a causes the main body 11 to pivot about the axis T2.

The control device 15 includes a light source controller 151 and a data processor 152. The light source controller 151 is connected to the laser light source 112 and the visible light source 114. The data processor 152 is connected to the CCD camera 111 and the laser light detector 113.

The light source controller 151 controls the laser light source 112 and the visible light source 114. With visible light emitted from the visible light source 114, a wide area including the sample S is irradiated. An image of the sample S observed through the sample window 162 is taken by the CCD camera 111, and sent through the data processor 152 to the output unit. Laser light beam emitted from the laser light source 112 is reflected by the half mirror 116, condensed by the condenser lens 141, and passes through the sample window 162, thereby causing the sample S to be irradiated. More specifically, the revealed surface of the semiconductor chip C of which the resin package of the sample S has been removed is irradiated with the laser light beam, and causes a bright spot on the sample S. If the surface of the semiconductor chip C is not tilted, the image of the sample S taken by the CCD camera 111 includes a clear image of the bright spot, and the light beam reflected by the surface of the semiconductor chip C returns along the same axis as that of the incident light, passes through the sample window 162 and the laser light condenser 14, is reflected by the half mirror 117 and detected by the laser light detector 113 as the largest luminance. The signal of the largest luminance detected by the laser light detector 113 is sent to the data processor 152. If the surface of the semiconductor chip C is tilted, the bright spot in the image of the sample S taken by the CCD camera 111 is distorted and the luminance decreases, which is detected by the data processor 152 as the sign of the tilt. For example, if the laser light beam has a circular cross-sectional shape, the bright spot is detected as a circle when there is no tilt of the sample S. When, on the contrary, there is a tilt of the sample S, the bright spot is detected as an ellipse and the luminance decreases.

Hereinafter, a method of correcting the tilt of the optical axis A1 is described with reference to FIG. 1 and FIG. 3. The control device 15 is not shown in FIG. 3 for simplicity.

In FIG. 1, the exposed surface of the semiconductor chip C is tilted after the resin package of the sample S has been removed with plasma. In this case, an optical axis A2 of the laser light beam reflected by the surface of the semiconductor chip C deviates from the optical axis A1 of the incident laser light beam, and the surface inspection apparatus 1 is unable to receive the reflected light beam.

Figure 3:
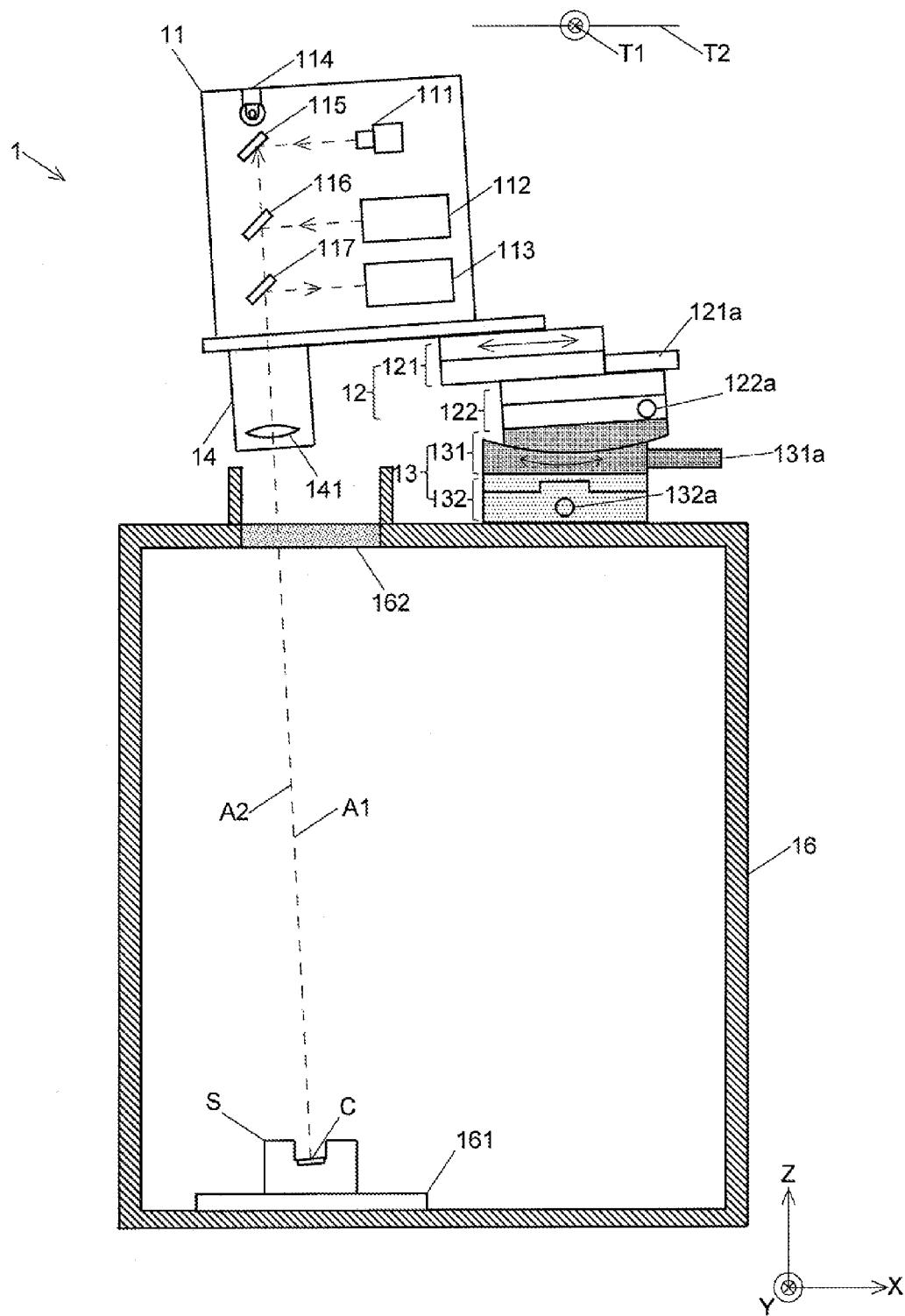
FIG. 3 is a schematic view of the surface inspection apparatus where reflected light correctly returns to a main body tilted by a cylindrical type two-axis gonio-stage.

To address this, an operator rotates the rotation handles 131a and/or 132a of the first gonio-stage 131 and/or the second gonio-stage 132 to gradually tilt optical axis A1 of the incident light while observing an image in a point irradiated by the light beam on the surface of the semiconductor chip C, and which is sent to the output unit, to thereby cause the optical axis A2 of the reflected light beam to return to the main body 11 (see FIG. 3). The fact that the optical axis A2 of the reflected light beam returns to the main body 11 can be determined by observation of a bright light spot of the reflected light beam through the CCD camera 111, or by observation of the shape of the bright spot in the image or the luminance of the bright spot as described before. Further fine adjustment allows the optical axis A2 of the reflected light beam to coincide with the optical axis A1 of the incident light, thereby correctly guiding the reflected light beam to the laser light detector 113.

If the optical axis A1 of the incident light beam is tilted, the irradiation point with the laser light beam on the semiconductor chip C moves. However, the XY stage 12 can bring the irradiation point to the original position. As a result, the optical axis A2 of the reflected light substantially coincides with the optical axis A1 of laser light emitted from the laser light source 112, and the target point can be continuously inspected.

Figure 4:
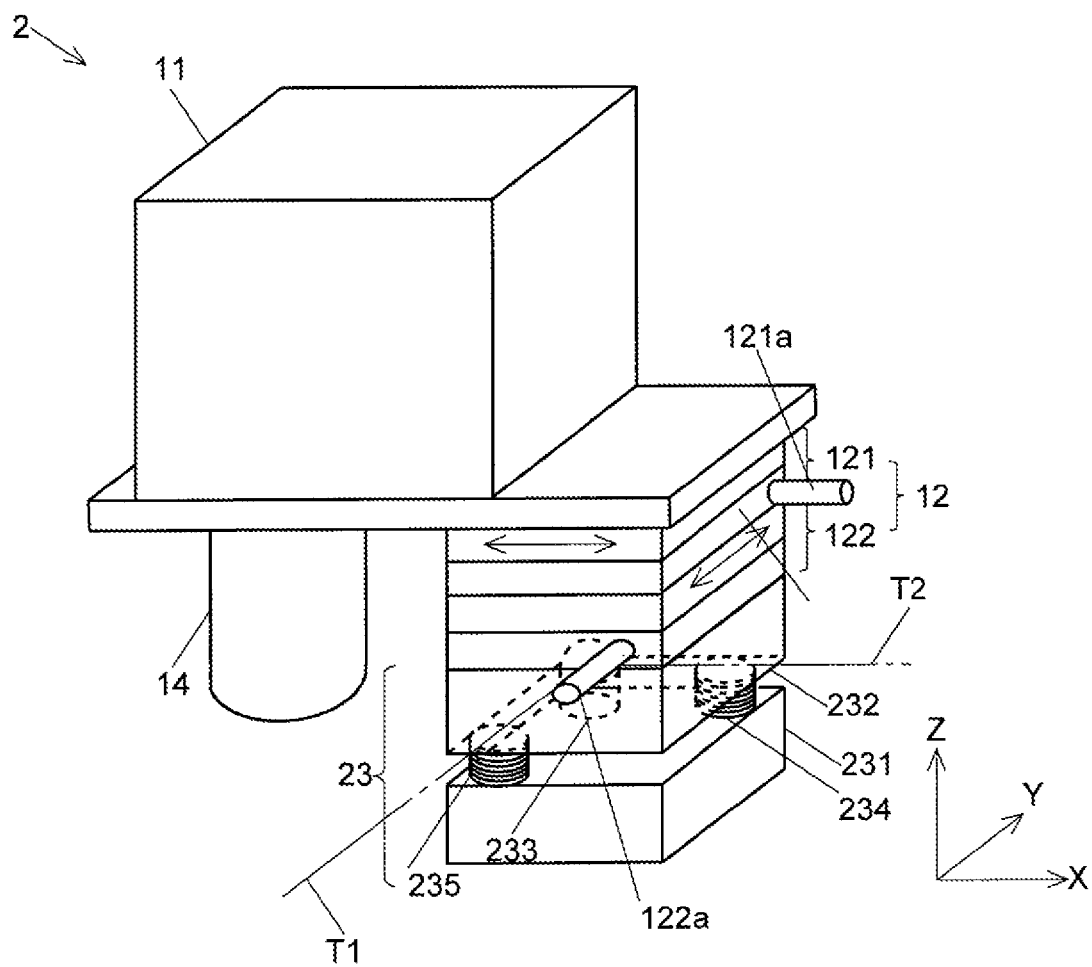
FIG. 4 is a perspective view of a main part of a surface inspection apparatus according to a second embodiment of the present invention.

FIG. 4 shows a perspective view of a surface inspection apparatus 2 according to a second embodiment of the present invention. The surface inspection apparatus 2 of this embodiment includes a plane tilting type two-axis gonio-stage 23 as the optical axis tilting mechanism. The main body 11 and other parts of the surface inspection apparatus 2 other than the plane tilting type two-axis gonio-stage 23 are the same as those of the surface inspection apparatus 1 of the first embodiment, and the explanation about them is thus omitted.

The plane tilting type two-axis gonio-stage 23 (hereinafter, simply referred to as "two-axis gonio-stage 23") of the surface inspection apparatus 2 of this embodiment includes a lower-disposed first stage 231, an upper-disposed second stage 232, a pivot 233 sandwiched between them, and a first liner motion mechanism 234 and a second liner motion mechanism 235 which are oppositely arranged at 90 degrees centered on the pivot 233. The first liner motion mechanism 234 and the second liner motion mechanism 235 are screws that change the distance between the first stage 231 and the second stage 232.

Figure 5:
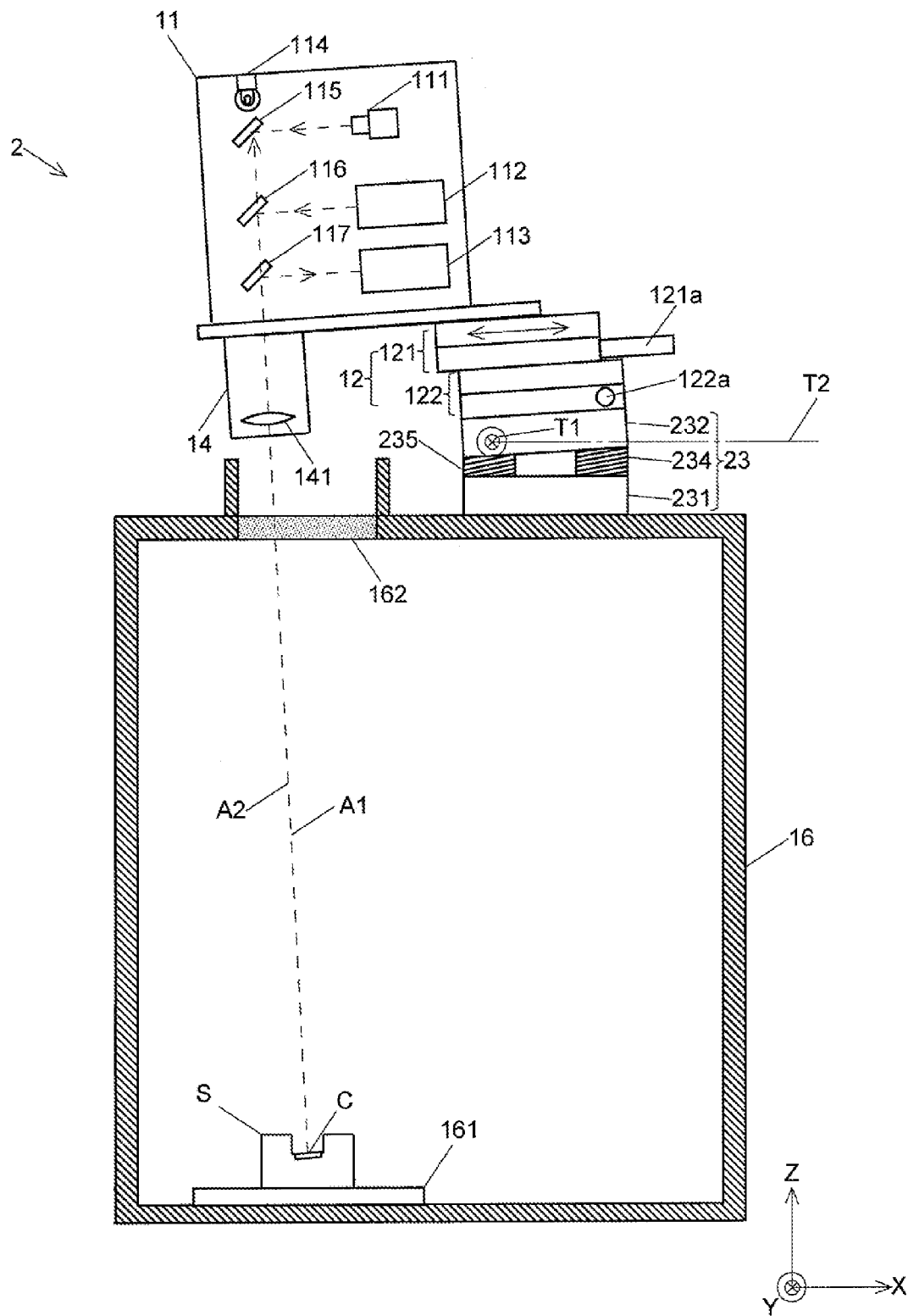
FIG. 5 is a schematic view of the surface inspection apparatus where a main body is tilted by a plane tilting type two-axis gonio-stage.

The lower end of the pivot 233 is fixed onto the first stage 231, and its distal end (upper end) is formed in a spherical shape so as to fit into a spherical recess provided in a bottom surface of the second stage 232. Changing the distance between the first stage 231 and the second stage 232 by the first liner motion mechanism 234 causes the main body 11 to tilt about the first tilting axis T1 with the contact portion of the distal end of the pivot 233 and the second stage 232 being as a pivot. Similarly, by the second liner motion mechanism 235, the main body 11 is tilted about the second tilting axis T2. A hydraulic or a pneumatic actuator may be employed instead of the liner motion mechanisms 234 and 235. FIG. 5 shows a result in which the first liner motion mechanism 234 and the second liner motion mechanism 235 tilt the optical axis A1 to enable the surface inspection apparatus 2 to receive the reflected light beam.

Figure 6:
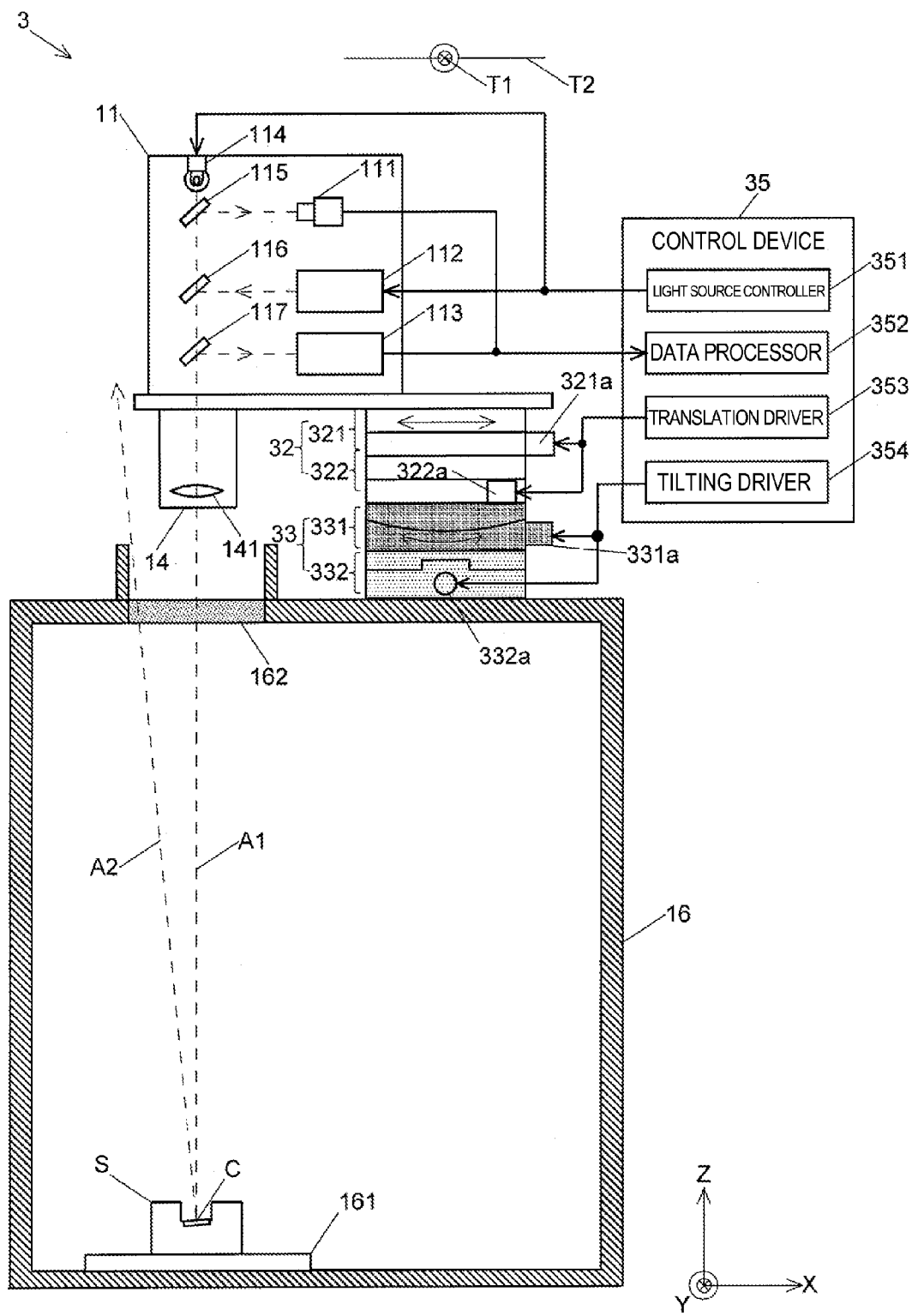
FIG. 6 is an overall configuration diagram of a surface inspection apparatus of a third embodiment of the present invention.

FIG. 6 shows a schematic overall configuration diagram of a surface inspection apparatus 3 according to a third embodiment of the present invention. The basic mechanism of the surface inspection apparatus 3 of this embodiment is the same as that of the surface inspection apparatus 1 of the first embodiment. Differing from the surface inspection apparatus 1 of the first embodiment, an XY stage 32 and a two-axis gonio-stage 33 are not manually driven but are automatically driven according to signals from the outside, and a control device 35 is provided with a translation driver 353 and a tilting driver 354. An X stage 321 and a Y stage 322 of the XY stage 32 are provided with an X direction driver 321a and a Y direction driver 322a, which translate the main body 11 according to signals from the translation driver 353 in the X direction and the Y direction, respectively. A first gonio-stage 331 and a second gonio-stage 332 of the two-axis gonio-stage 33 are provided with a first axis driver 331a and a second axis driver 332a, which rotate the main body 11 according to signals from the tilting driver 354 about a first tilting axis T1 and a second tilting axis T2, respectively.

Operations of the control device 35 in the surface inspection apparatus 3 of this embodiment are described. A light source controller 351 of the control device 35 causes the laser light source 112 to emit laser light, and causes the visible light source 114 to emit visible light. The sample S is irradiated with both lights passing through the sample window 162. An image in a wide area including the sample S inside the vacuum chamber, which is formed by reflected light of the visible light is taken by the CCD camera 111, is sent to a data processor 352, and subjected to the image analysis. The data processor 352 detects a portion of the taken image having a luminance larger than a first predetermined value. This identifies the point on the semiconductor chip C revealed from the sample S at which the laser light beam is irradiated. The irradiation point may be identified based not only on the luminance but also on the color (wavelength) of the laser light beam. Of course, they may be simultaneously used.

Laser light beam emitted from the laser light source 112 is reflected by the surface of the semiconductor chip C, and returns to the main body 11. However, as shown in FIG. 6, in the case where the surface of the semiconductor chip C is not perpendicular to the optical axis A1 of the incident laser light beam, the reflected light beam passes along an optical axis A2 deviating from the optical axis A1, which prevents the light beam from being detected by the laser light detector 113. In this case, the luminance of the point irradiated with the laser light in the image taken by the CCD camera 111 is larger than the first predetermined value but lower than a second predetermined value that is set in consideration of the luminance when the laser light beam reflected by the sample directly enters the CCD camera 111. The control device 35 drives the two-axis gonio-stage 33 through the tilting driver 354 and drives the XY stage 32 through the translation driver 353, thereby causing the luminance at the point irradiated with the laser light beam to have a value higher than the second predetermined value. When the luminance of the point irradiated with the laser light becomes higher than the second predetermined value, the control device 35 stops driving the two-axis gonio-stage 33 and the XY stage 32 judging that the optical axis A2 coincides with the optical axis A1 and the reflected light of the laser light beam from the surface of the sample S enters the laser light detector 113.

Figure 7:
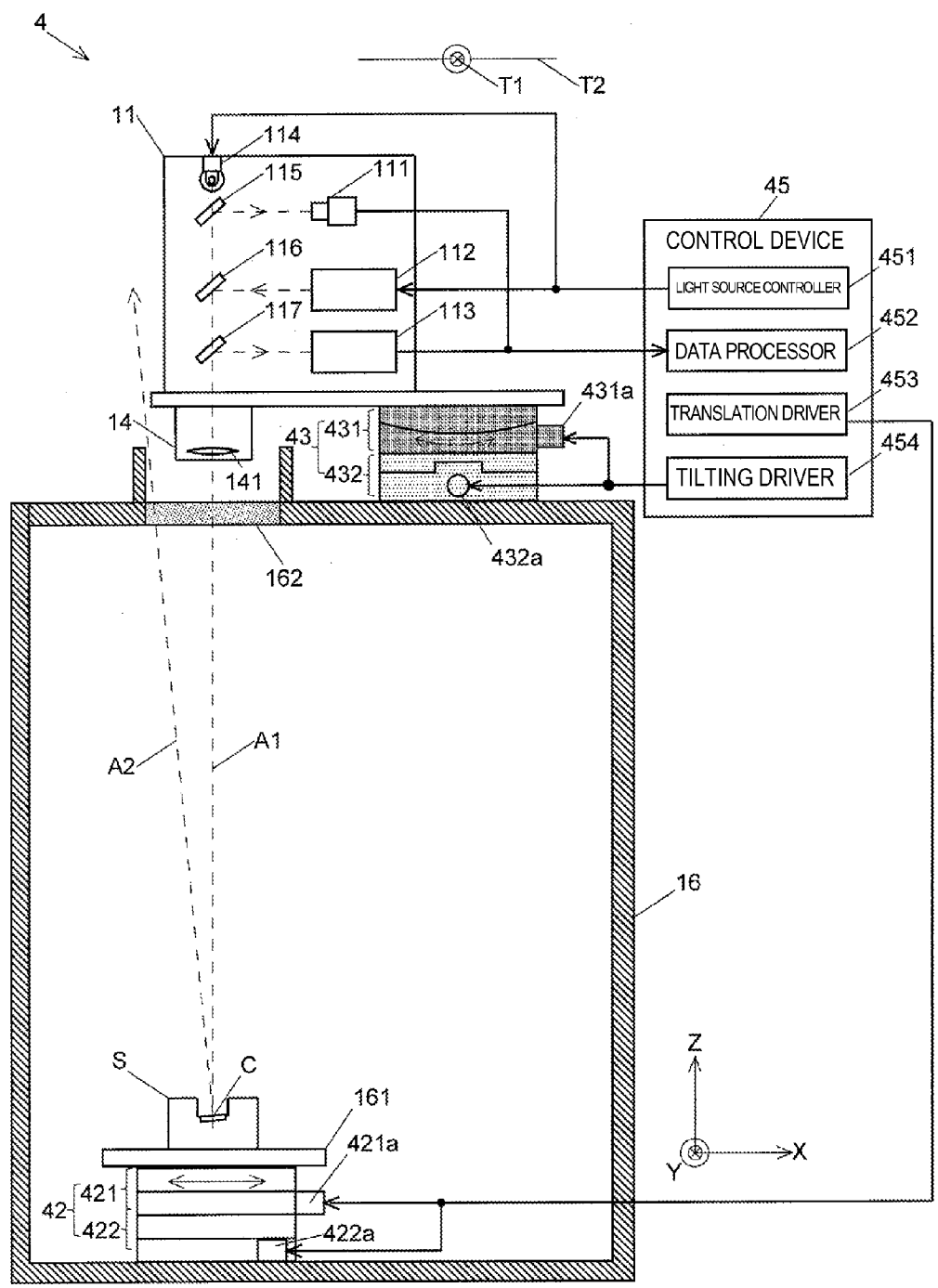
FIG. 7 is an overall configuration diagram of a surface inspection apparatus according to a fourth embodiment of the present invention.

FIG. 7 shows a schematic overall configuration diagram of a surface inspection apparatus 4 according to a fourth embodiment of the present invention. The surface inspection apparatus 4 of this embodiment is the same as the surface inspection apparatus 3 of the third embodiment in that a two-axis gonio-stage 43 is automatically driven according to signals from the outside. Differing from the surface inspection apparatus 3 of the third embodiment, an automatically driven XY stage 42 that is driven according to the signals from the outside is equipped not with the main body 11 but with the sample stage 161. An X stage 421 and a Y stage 422 of the XY stage 42 are provided with an X direction drive input terminal 421a and a Y direction drive input terminal 422a respectively, and the both stages translate the sample stage 161 according to signals from the translation driver 453 in the X direction and the Y direction, respectively. A first gonio-stage 431 and a second gonio-stage 432 of the two-axis gonio-stage 43 are provided with a first axis driver 431a and a second axis driver 432a, which rotate the main body 11 according to signals from a tilting driver 454 about a first tilting axis T1 and a second tilting axis T2, respectively.

Operations of a control device 45 in the surface inspection apparatus 4 of this embodiment are described. A light source controller 451 of the control device 45 causes the laser light source 112 to emit laser light, and causes the visible light source 114 to emit visible light. The sample S is irradiated with the both lights passing through the sample window 162. An image in a wide area including the sample S taken by the CCD camera 111 with the visible light is sent to a data processor 452, and subjected to an image analysis. The data processor 452 detects a portion of the taken image having a luminance larger than the first predetermined value. This identifies the point on the semiconductor chip C revealed from the sample S at which the laser light beam is irradiated. The irradiation point may be identified based not only on the luminance but also on the color (wavelength) of the laser light beam. Of course, they may be simultaneously used.

Laser light beam emitted from the laser light source 112 is reflected by the surface of the semiconductor chip C, and returns to the main body 11. However, as shown in FIG. 7, in the case where the surface of the semiconductor chip C is not perpendicular to the optical axis A1 of the incident laser light beam, the reflected light beam passes along an optical axis A2 deviating from the optical axis A1, which prevents the light beam from being detected by the laser light detector 113. In this case, the luminance of the point irradiated with the laser light beam in the image taken by the CCD camera 111 is at least the first predetermined value but lower than the second predetermined value that is set taken into account the luminance when the laser light beam reflected by the sample S directly enters the CCD camera 111. The control device 45 drives the two-axis gonio-stage 43 through the tilting driver 454 as well as driving the XY stage 42 through the translation driver 453, thereby causing the luminance at the point irradiated with the laser light to have a value higher than the second predetermined value. At the point when the luminance of the point irradiated with the laser light becomes higher than the second predetermined value, the control device 45 stops driving the two-axis gonio-stage 43 and the XY stage 42 judging that the optical axis A2 coincides with the optical axis A1, and the reflected light beam of the laser light from the surface of the sample S enters the laser light detector 113.

The surface inspection apparatuses 3 and 4 of the third and fourth embodiments tilt the optical axis A1 of the laser light beam by analyzing the image of the sample. Alternatively, the tilt of the optical axis A1 of the laser light beam may be directly measured. In one of such methods, the stages 331 and 332 of the axes of the two-axis gonio-stage 33 are provided with respective rotating position sensors. According to another method, a sensor for detecting the tilt degree from a vertical line or a horizontal plane is provided for the main body 11.

Four embodiments have been described above. However, the present invention is not limited to these embodiments. It is apparent that configurations appropriately added or modified within a scope of the gist are encompassed in the claims of the present patent application.

REFERENCE SIGNS LIST 1, 2, 3, 4 . . . Surface Inspection Apparatuses
11 . . . Main Body
111 . . . CCD Camera
112 . . . Laser Light Source
113 . . . Laser Light Detector
114 . . . Visible Light Source
115, 116, 117 . . . Half Mirror
12, 32, 42 . . . XY Stage
121, 321, 421 . . . X Stage
121a . . . X direction translation handle
321a, 421a . . . X Direction Driver
122, 322, 422 . . . Y Stage
122a . . . Y direction translation handle
322a, 422a . . . Y Direction Driver
13, 33, 43 . . . Cylindrical Type Two-Axis Gonio-Stage
131, 331, 431 . . . First Gonio-Stage
131a . . . First rotation handle
331a, 431a . . . First Axis Driver
132, 332, 432 . . . Second Gonio-Stage
132a . . . Second rotation handle
332a, 432a . . . Second Axis Driver
14 . . . Laser Light Condenser
141 . . . Condenser Lens
15, 35, 45 . . . Control Device
151, 351, 451 . . . Light Source Controller
152, 352, 452 . . . Data Processor
353, 453 . . . Translation Driver
354, 454 . . . Tilting Driver
16 . . . Vacuum Chamber
161 . . . Sample Stage
162 . . . Sample Window
23 . . . Planar Tilt Type Two-Axis Gonio-Stage
231 . . . First Stage
232 . . . Second Stage
233 . . . Pivot

234 . . . First Liner motion mechanism
235 . . . Second Liner motion mechanism
A1, A2 . . . Optical Axis
T1 . . . First Tilting Axis
T2 . . . Second Tilting Axis
S . . . Sample
C . . . Semiconductor Chip

The invention claimed is:

1. A light beam measuring instrument comprising:
    a light beam source for emitting a light beam toward an object through a beam condenser;
    a light beam detector for detecting the light beam that is reflected by a surface of the object and passes back again through light beam condenser;
    a first optical-axis-tilting mechanism that tilts the light beam source about a first tilting axis lying in a plane unparallel to an optical axis of the light beam emitted from the light beam source; and
    a second optical-axis-tilting mechanism that tilts the light beam source about a second tilting axis lying in the plane and unparallel to the first tilting axis.

2. The light beam measuring instrument according to claim 1, further comprising a translation mechanism that translates the light beam source.

3. The light beam measuring instrument according to claim 1, further comprising a translation mechanism that translates the object.

4. The light beam measuring instrument according to claim 1, wherein the optical axis tilting mechanism is a cylindrical type two-axis gonio-stage.

5. The light beam measuring instrument according to claim 1, wherein the optical axis tilting mechanism is a plane tilting type two-axis gonio-stage.

6. The light beam measuring instrument according to claim 2, further comprising:
    a tilt detector that detects a tilt of the optical axis of the light beam emitted from the light beam source;
    a translation driver that drives the translation mechanism; and
    an irradiation position controller that controls the translation driver based on the tilt.

7. The light beam measuring instrument according to claim 6, wherein the tilt detector detects the tilt at the optical axis tilting mechanism.

8. The light beam measuring instrument according to claim 6, further comprising an imager that takes an image of the object, and the tilt detector detects the tilt based on the image.

9. A plasma processing apparatus, comprising the light beam measuring instrument according to claim 1.

* * * * *